(12) United States Patent
Zhang (10) Patent No.: US 10,579,037 B1
(45) Date of Patent: Mar. 3, 2020

(54) POSITIONING METHOD AND APPARATUS (71) Applicant: Alibaba Group Holding Limited, Grand Cayman (KY)

(72) Inventor: Jie Zhang, Hangzhou (CN)

(73) Assignee: Alibaba Group Holding Limited, Cayman Islands (KY)

( * ) Notice: Subject to any disclaimer, the term of this patent is extended or adjusted under 35 U.S.C. 154(b) by 442 days.

(21) Appl. No.: 15/381,899

(22) Filed: Dec. 16, 2016

(30) Foreign Application Priority Data

Dec. 17, 2015 (CN) .......................... 2015 1 0954979

(51) Int. Cl.
G05B 19/19 (2006.01)
G05B 19/406 (2006.01)
G01C 22/00 (2006.01)

(52) U.S. Cl.
CPC ........... *G05B 19/19* (2013.01); *G01C 22/006* (2013.01); *G05B 19/406* (2013.01); *G05B 2219/24015* (2013.01); *G05B 2219/42019* (2013.01)

(58) Field of Classification Search
CPC ........ G01C 22/006; G01C 5/06; B60R 25/20; G01B 21/02
See application file for complete search history.

(56) References Cited

U.S. PATENT DOCUMENTS

| 758,405 | A | 4/1904 | Bartel | |
| 7,653,508 | B1 * | 1/2010 | Kahn | ..................... G01B 21/02 33/700 |
| 9,939,264 | B2 * | 4/2018 | Barfield | .................... G01C 5/06 |
| 2007/0143068 | A1 | 6/2007 | Pasolini et al. | |
| 2007/0273553 | A1 * | 11/2007 | Albrecht | ................. B60R 25/20 340/932.2 |
| 2010/0007557 | A1 | 1/2010 | Nagahara et al. | |
| 2011/0300835 | A1 | 12/2011 | Kasama | |
| 2013/0197857 | A1 | 8/2013 | Lu et al. | |

(Continued)

FOREIGN PATENT DOCUMENTS

CN 102419180 A 4/2012
CN 103413464 A 11/2013

(Continued)

OTHER PUBLICATIONS

PCT Search Report and Written Opinion dated Jun. 20, 2017 for PCT Application No. PCT/US16/67272, 12 pages.

(Continued)

*Primary Examiner* — Ziaul Karim
(74) *Attorney, Agent, or Firm* — Lee & Hayes, P.C.

(57) ABSTRACT

A positioning method is disclosed. The positioning method includes collecting at least two types of sensor data reflecting a motion state of a terminal device in a step-counting period in real time; separately filtering the at least two types of sensor data to obtain filtered sensor data; step-counting a user holding the terminal device based on the filtered sensor data to obtain a distance and a direction of movement of the user in the step-counting period; and correcting current position information of the user based on the distance and the direction of the movement of the user in the step-counting period to implement positioning of the user. The technical solution provided in the present disclosure can be adopted to improve the accuracy of indoor positioning.

11 Claims, 7 Drawing Sheets (56) References Cited

U.S. PATENT DOCUMENTS

| | | | |
|---|---|---|---|
| 2013/0311133 A1* | 11/2013 | Kordari | G01C 22/006 |
| | | | 702/160 |
| 2014/0288822 A1 | 9/2014 | Morrison et al. | |
| 2014/0305204 A1* | 10/2014 | Hong | A63B 71/06 |
| | | | 73/504.08 |
| 2015/0198625 A1 | 7/2015 | Ghose et al. | |
| 2015/0260542 A1 | 9/2015 | Gasparini et al. | |
| 2016/0095538 A1 | 4/2016 | Lee et al. | |
| 2016/0356593 A1 | 12/2016 | Huang et al. | |
| 2019/0063949 A1* | 2/2019 | Liao | G01C 22/006 |

FOREIGN PATENT DOCUMENTS

| | | |
|---|---|---|
| CN | 104061934 A | 9/2014 |
| CN | 104089624 A | 10/2014 |
| CN | 104251699 A | 12/2014 |
| CN | 104977006 A | 10/2015 |

OTHER PUBLICATIONS

Machine translation (English) of the First Chinese Office Action dated Aug. 1, 2019 for Chinese Patent Application No. 201510954979. 0, a counterpart foreign application of U.S. Appl. No. 15/381,899, 14 pages.

Machine translation (English) Chinese Search Report dated Aug. 1, 2019, for Chinese Patent Application No. 201510954979.0, a counterpart foreign application of U.S. Appl. No. 15/381,899, 5 pages.

The First Chinese Search Report dated Jul. 23, 2019, for Chinese Patent Application No. 2015109549790, 2 pages.

\* cited by examiner

POSITIONING METHOD AND APPARATUS

CROSS REFERENCE TO RELATED PATENT APPLICATION

This application claims foreign priority to Chinese Patent Application No. 201510954979.0 filed on Dec. 17, 2015, entitled "Positioning Method and Apparatus", which is hereby incorporated by reference in its entirety.

TECHNICAL FIELD

The present disclosure relates to the field of communication technologies, and in particular, to positioning methods and apparatuses.

BACKGROUND

With the development of science and technology, and the popularization of MEMS (Micro-Electro-Mechanical System) inertial sensors, an increasing number of electronic devices such as pedometers, cell phones, and smart watches are provided with a gyroscope and an accelerometer, which thereby help a user to conduct statistics and collection of motion information, analyze a running state of the user, and conduct indoor positioning for the user.

Due to the surrounding issues or intrinsic problems of inertial sensors, collected sensor data includes noises, thus resulting in a low degree of accuracy of inertial sensor-based indoor positioning.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter. The term "techniques," for instance, may refer to device(s), system(s), method(s) and/or computer-readable instructions as permitted by the context above and throughout the present disclosure.

Multiple aspects of the present disclosure provide a positioning method and an apparatus thereof to improve the accuracy of indoor positioning.

In an aspect of the present disclosure, a positioning method is provided, which may include collecting at least two types of sensor data that reflect a motion state of a terminal device in a step-counting period in real time; individually filtering the at least two types of sensor data to obtain filtered sensor data; performing step-counting of a user holding the terminal device based on the filtered sensor data to obtain a distance and a direction of movement of the user in the step-counting period; and correcting current position information of the user based on the distance and the direction of the movement of the user in the step-counting period to implement positioning of the user.

In another aspect of the present disclosure, a positioning apparatus is provided, which may include a state collection module to collect at least two types of sensor data that reflect a motion state of a terminal device in a step-counting period in real time; a filtering module to individually filter the at least two types of sensor data to obtain filtered sensor data; a step-counting module configured to perform step-counting of a user holding the terminal device based on the filtered sensor data to obtain a distance and a direction of movement of the user in the step-counting period; and a positioning module to correct current position information of the user based on the distance and the direction of the movement of the user in the step-counting period to implement positioning of the user.

In the present disclosure, at least two types of sensor data that are able to reflect a motion state of a terminal device are collected in a step-counting period in real time. The collected sensor data is filtered, and steps of a user holding the terminal device is counted based on the filtered sensor data to obtain a distance and a direction of movement of the user in the step-counting period, by which current position information of the user is corrected to implement positioning of the user. On the one hand, the positioning method provided in the present disclosure uses multiple types of sensor data to implement multi-information fusion, thereby facilitating an improvement in the positioning accuracy due to a relatively abundant amount of information. On the other hand, filtering the multiple types of sensor data can remove noises that are included in the sensor data, thereby enabling the positioning accuracy to be improved.

BRIEF DESCRIPTION OF THE DRAWINGS

In order to explain technical solutions of exemplary embodiments of the present disclosure more clearly, drawings that are used for describing the embodiments or existing technologies are briefly described herein. Apparently, the described drawings represent a few embodiments of the present disclosure, and other drawings can be obtained by one skilled in the art based on these drawings without making any creative effort.

DETAILED DESCRIPTION

In order to make the objectives, technical solutions and advantages of the embodiments of the present disclosure more clear, the technical solutions in the embodiments of the present disclosure will be described clearly and completely in conjunction with the accompanying drawings of the embodiments of the present disclosure. Apparently, the described embodiments represent some and not all of the embodiments of the present disclosure. Based on the embodiments of the present disclosure, all other embodiments derived by one of ordinary skill in the art without making any creative effort shall fall in the scope of protection of the present disclosure.

Figure 1:
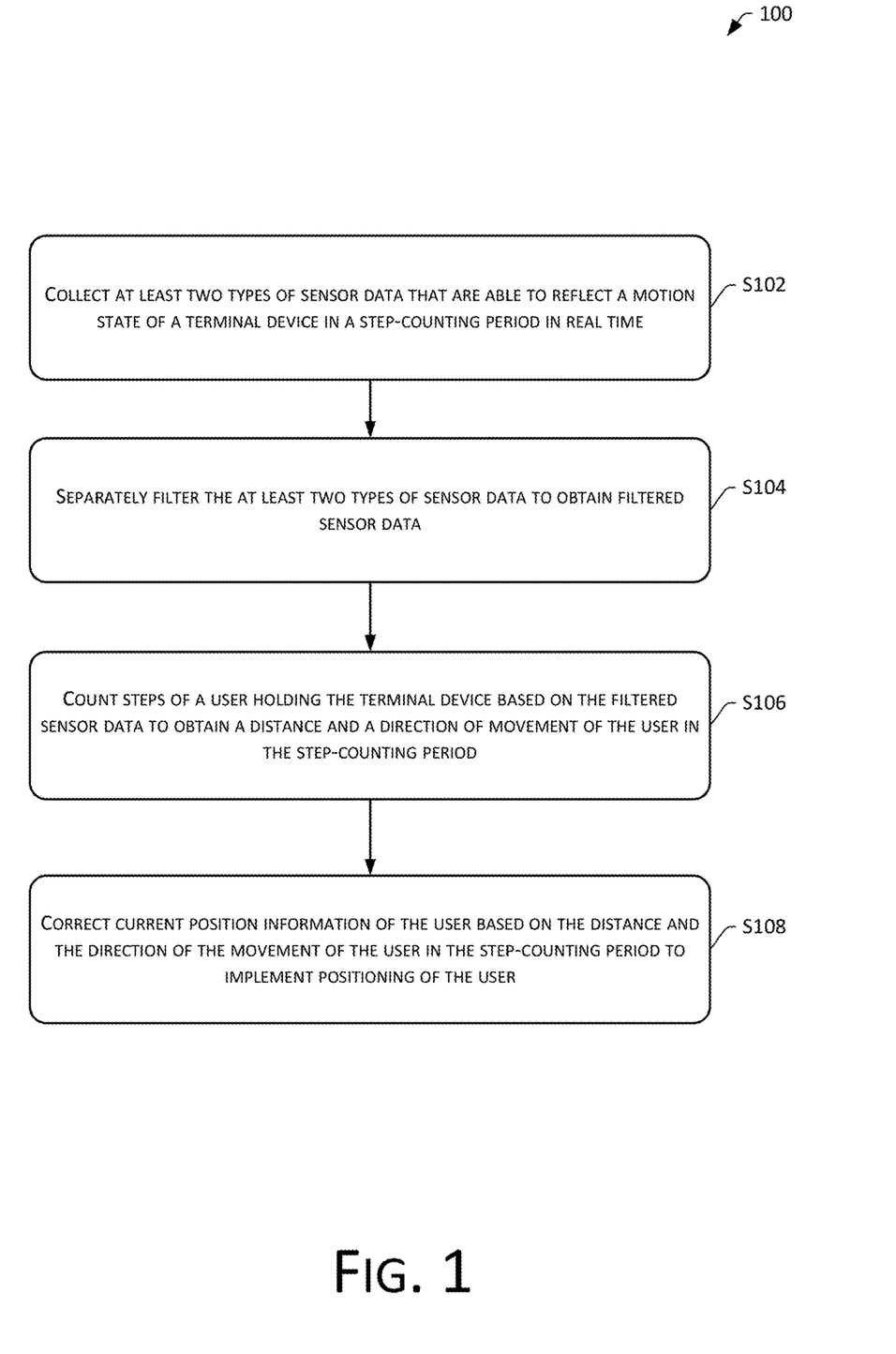
FIG. 1 is a flowchart of a positioning method according to embodiments of the present disclosure.

FIG. 1 is a flowchart of a positioning method 100 according to the embodiments of the present disclosure. As shown in FIG. 1, the method 100 may include the following operations.

S102 collects at least two types of sensor data that are able to reflect a motion state of a terminal device in a step-counting period in real time.

S104 separately filters the at least two types of sensor data to obtain filtered sensor data.

S106 counts steps of a user holding the terminal device based on the filtered sensor data to obtain a distance and a direction of movement of the user in the step-counting period.

S108 corrects current position information of the user based on the distance and the direction of the movement of the user in the step-counting period to implement positioning of the user.

In implementations, the positioning method may be executed by a positioning device. A principle thereof may include, combining multiple types of sensor data and filtering the multiple types of sensor data during positioning to improve the accuracy of positioning. The positioning processing performed by the example positioning method provided in the present disclosure produces a positioning result with a high degree of accuracy, and is applicable to an indoor positioning scenario, which fulfills requirements of indoor positioning. Nevertheless, the present disclosure is not limited to indoor positioning scenarios.

In implementations, a step-counting period is set up in advance, such that steps of a user are counted periodically, and the user is positioned based on a step-counting result. A size of the step-counting period may be determined based on specific positioning requirements, which is, but not limited to, 500 milliseconds, 1 second, 3 seconds, 5 seconds, etc., for example. For the ease of description, a current step-counting period is used as an example, and at least two types of sensor data that can reflect a motion state of a terminal device are collected in real time in the current step-counting period.

A terminal device is generally provided with multiple inertial sensors, such as an acceleration sensor, a gyroscope, and an electronic compass, etc. These inertial sensors can detect a motion state of the terminal device. Generally, different inertial sensors may be used for detecting different state parameters. For example, an acceleration sensor can detect a value of an acceleration of the terminal device. A gyroscope can detect a value of an angular velocity of the terminal device. An electronic compass can detect a value of a magnetic field vector of the terminal device.

In implementations, the step-counting period may be implemented using a sliding window. In implementations, a size of the sliding window may be set as the step-counting period. For example, the size of the sliding window may be set as 500 milliseconds, 1 second, 3 seconds, 5 seconds, etc. Accordingly, sensor data that reflects a motion state of the terminal device may be collected in real time, and the collected sensor data is sent to the sliding window. When the sliding window is filled, this means that the step-counting period is reached. The sensor data within the sliding window may then be obtained, and subsequent operations S104–S108 may be performed to perform positioning of the user based on a step-counting result of the user in the step-counting period.

Since the surrounding issues or intrinsic problems of sensors may generate noises in sensor data, the at least two types of sensor data are filtered to obtain filtered sensor data after the at least two types of sensor data are obtained, in order to improve the accuracy of positioning. For example, each type of sensor data may be, but not limited to, low-pass filtered and/or mean-filtered.

In implementations, a low-pass filtering algorithm may include the following formula:

$$Y(n)=a*X(n)+(1-a)*Y(n-1)$$

In the above formula, $X(n)$ denotes sensor data collected in a current step-counting period. $Y(n-1)$ denotes filtered sensor data that is obtained after filtering in a previous step-counting period. $a$ denotes a filter coefficient, and has a value generally much less than 1. $Y(n)$ denotes filtered sensor data that is obtained after filtering in the current step-counting period.

After filtered sensor data is obtained, the positioning device may step-count a user holding the terminal device to obtain a distance and a direction of movement of the user in the current step-counting period, and correct current position information of the user based on the distance and the direction of the movement of the user in the current step-counting period to achieve accurate positioning of the user.

In implementations, the sensor data that reflects the motion state of the terminal device may include acceleration values and angular velocity values. Accordingly, the operation S102 may include collecting acceleration values and angular velocity values of the terminal device in the current step-counting period in real time. For example, an acceleration sensor of the terminal device may collect acceleration values of the terminal device in real time, and a gyroscope of the terminal device may collect angular velocity values of the terminal device in real time. The positioning device may request to obtain the acceleration values and the angular velocity values of the terminal device from the acceleration sensor and the gyroscope of the terminal device respectively.

Other than acceleration values and angular velocity values, the sensor data that reflects the motion state of the terminal device may further include magnetic field vector values of the terminal device. An electronic compass of the terminal device may collect magnetic field vector values of the terminal device in real time. The positioning device may request to obtain the magnetic field vector values of the terminal device from the electronic compass of the terminal device.

It should be noted that magnetic field vector values of the terminal device may be converted to angular velocity values and may be identical to the angular velocity values. Therefore, a description of sensor data that reflects a motion state of a terminal device to include acceleration values and angular velocity values is mainly used as an example in the present embodiment. To some extent, acceleration value(s) of the terminal device may reflect whether a user moves and a speed of movement, and angular velocity value(s) of the terminal device may reflect a moving direction of the user.

Accordingly, an implementation of individually filtering the at least two types of sensor data to obtain filtered sensor data, i.e., the operation S104, may include separately filtering acceleration values and angular velocity values to obtain filtered acceleration values and filtered angular velocity values.

Figure 2:
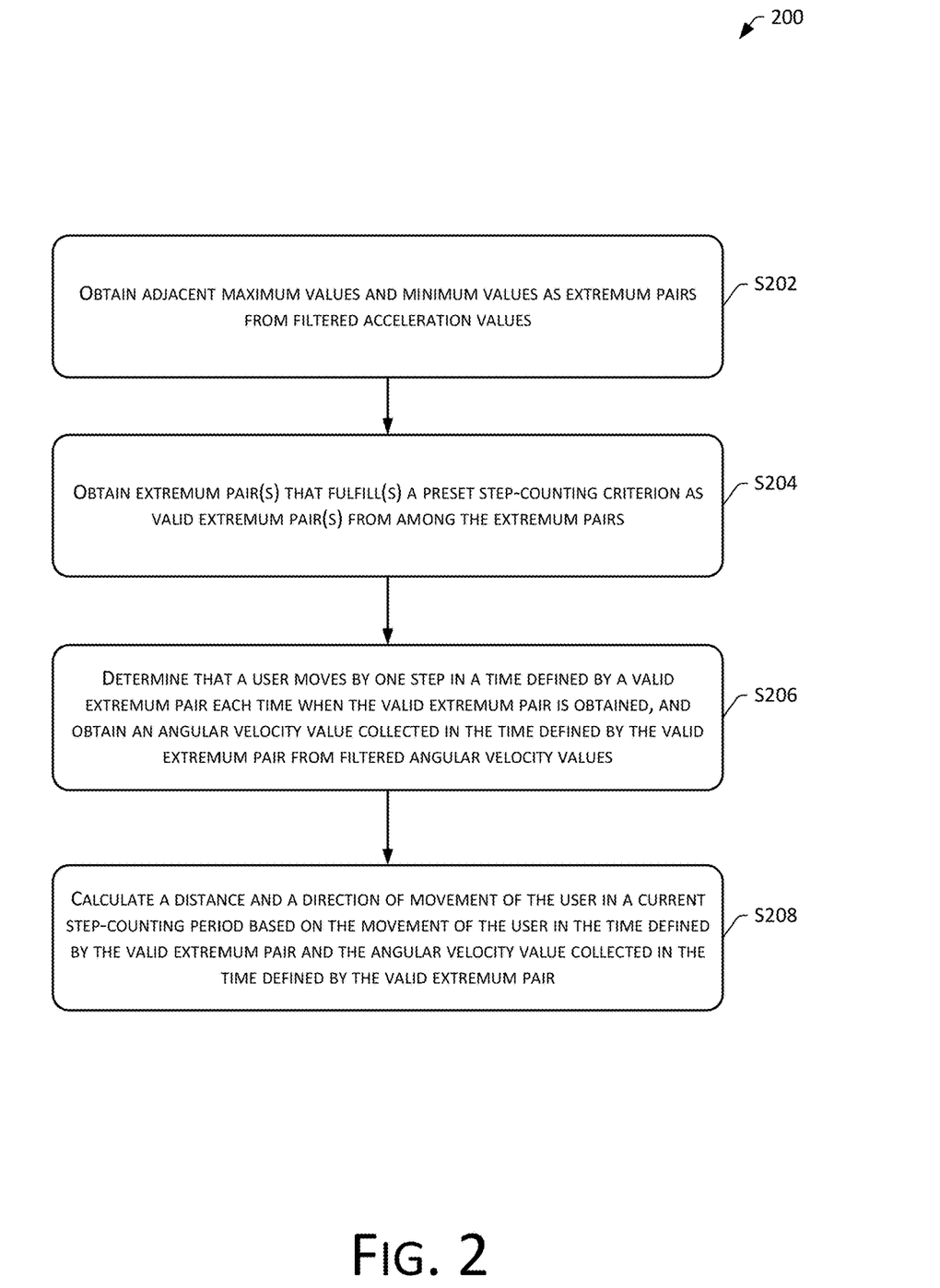
FIG. 2 is a flowchart of an example implementation of S103 according to the embodiments of the present disclosure.

Furthermore, an implementation of step-counting a user holding the terminal device based on the filtered sensor data to obtain a distance and a direction of movement of the user in the current step-counting period, i.e., the operation S106, is shown in FIG. 2, and may include the following operations.

S202 obtains adjacent maximum values and minimum values as extremum pairs from filtered acceleration values.

Figure 3:
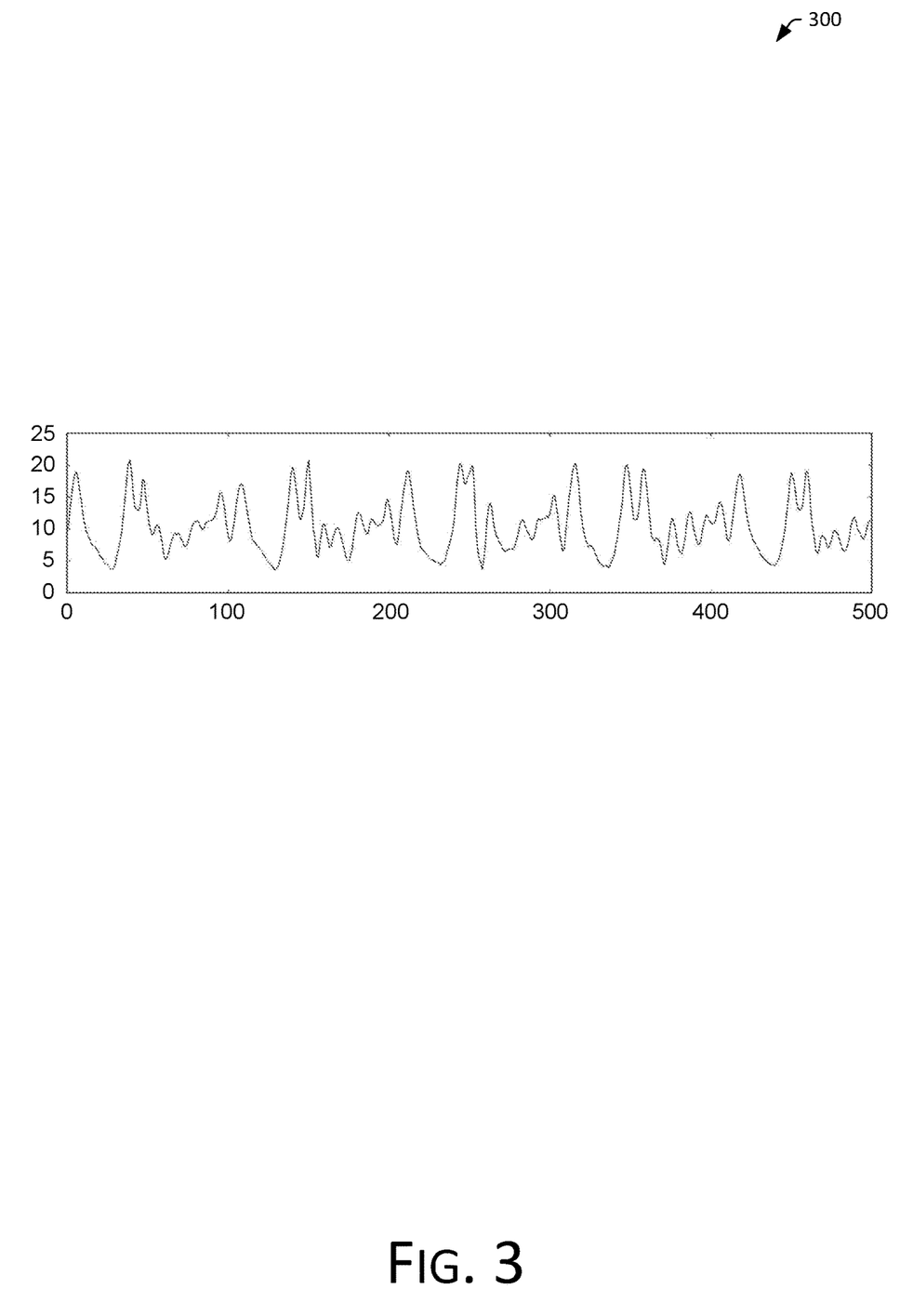
FIG. 3 is a schematic diagram of a waveform of filtered acceleration values according to the embodiments of the present disclosure.

The obtained extremum pairs refer to extremum pairs in a current step-counting period herein. FIG. 3 shows a schematic diagram of a waveform 300 of filtered acceleration values in a step-counting period. In implementations, obtaining the adjacent maximum values and minimum values as the extremum pairs from the filtered acceleration values refers to an act of counting how many peak values in a waveform diagram as shown in FIG. 3, for example, in which two adjacent peak values are considered as an extremum pair.

S204 obtains extremum pair(s) that fulfill(s) a preset step-counting criterion as valid extremum pair(s) from among the extremum pairs.

Generally, acceleration value(s) of a terminal device may reflect whether a user moves. Theoretically, each time when an extremum pair is found in acceleration values of the terminal device, this indicates that the user moves by one step. In reality, a situation that a user does not move and a terminal device experiences an acceleration exists, e.g., in a change in a position of the terminal device that is caused by the user turning around, lifting an arm, etc. In implementations, in order to identify whether a user moves in a more accurate manner, a step-counting criterion is set in advance, and extremum pairs are filtered according to the step-counting criterion to obtain valid extremum pair(s), and a valid extremum pair is used for indicating that a user moves by one step.

As can be known from a real situation when a user moves, each time when the user moves by one step, a certain period of time and a certain amplitude are needed. The period of time needed when the user moves by one step may be indicated by a time defined by an extremum pair, and the amplitude of the movement of the user may be indicated by an amplitude of the extremum pair. The time defined by the extremum pair refers to a period of time between a time point when a maximum value in the extremum pair appears and a time point when a minimum value in the extremum pair appears. Accordingly, in implementations, the preset step-counting criterion may include an extremum range and a time range. An example extremum range may include, but not limited to: [g+0.5, g+5], wherein g denotes a gravity coefficient, and is a constant. A time range may include, but not limited to, [300 ms, 1100 ms], for example. The time range may correspond to, but not limited to, an average value obtained by conducting statistics on time needed for one-step movement of a large number of users.

Accordingly, a determination may be made as to whether absolute values of a maximum value and a minimum value in an extremum pair are located in an extremum range and whether a time defined by the extremum pair is located in a time range for each extremum pair. If determination results thereof are both affirmative, this indicates that an amplitude of the maximum value and the minimum value and the time defined by the respective extremum pair both satisfy a situation of one-step movement of the user. Therefore, the respective extremum pair is determined to be a valid extremum pair, thereby determining that the user moves by one step in the time defined by the extremum pair. If one of the determination results is negative, a determination is made that the user does not move.

It should be noted that the operation of determining whether absolute values of a maximum value and a minimum value in an extremum pair are both located in an extremum range and the operation of determining whether a time defined by the extremum pair is located in a time range may be executed in a random order, and may also be executed in parallel.

Figure 4:
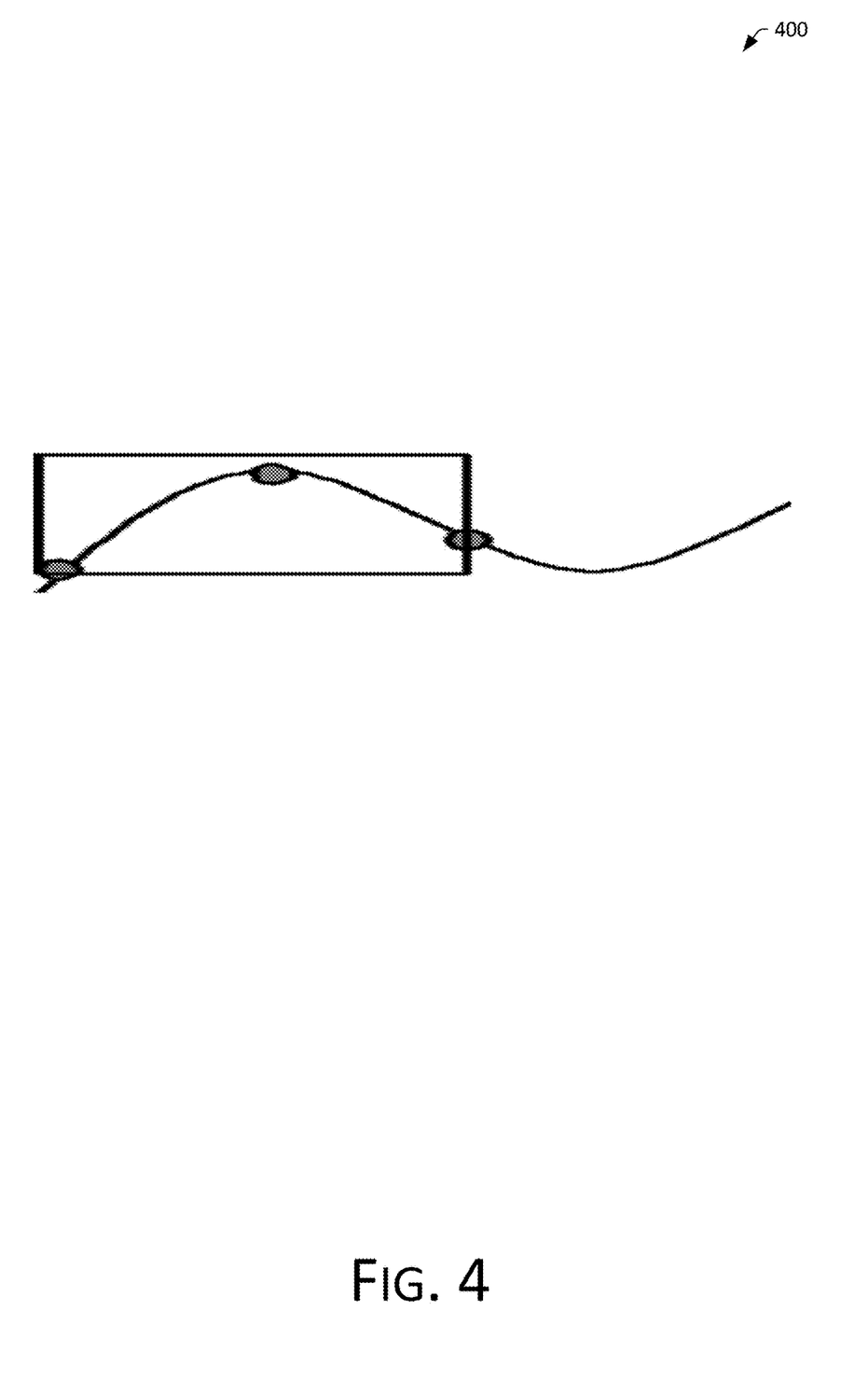
FIG. 4 is a schematic diagram of a minimum value appearing at a left border of a sliding window according to the embodiments of the present disclosure.
Figure 5:
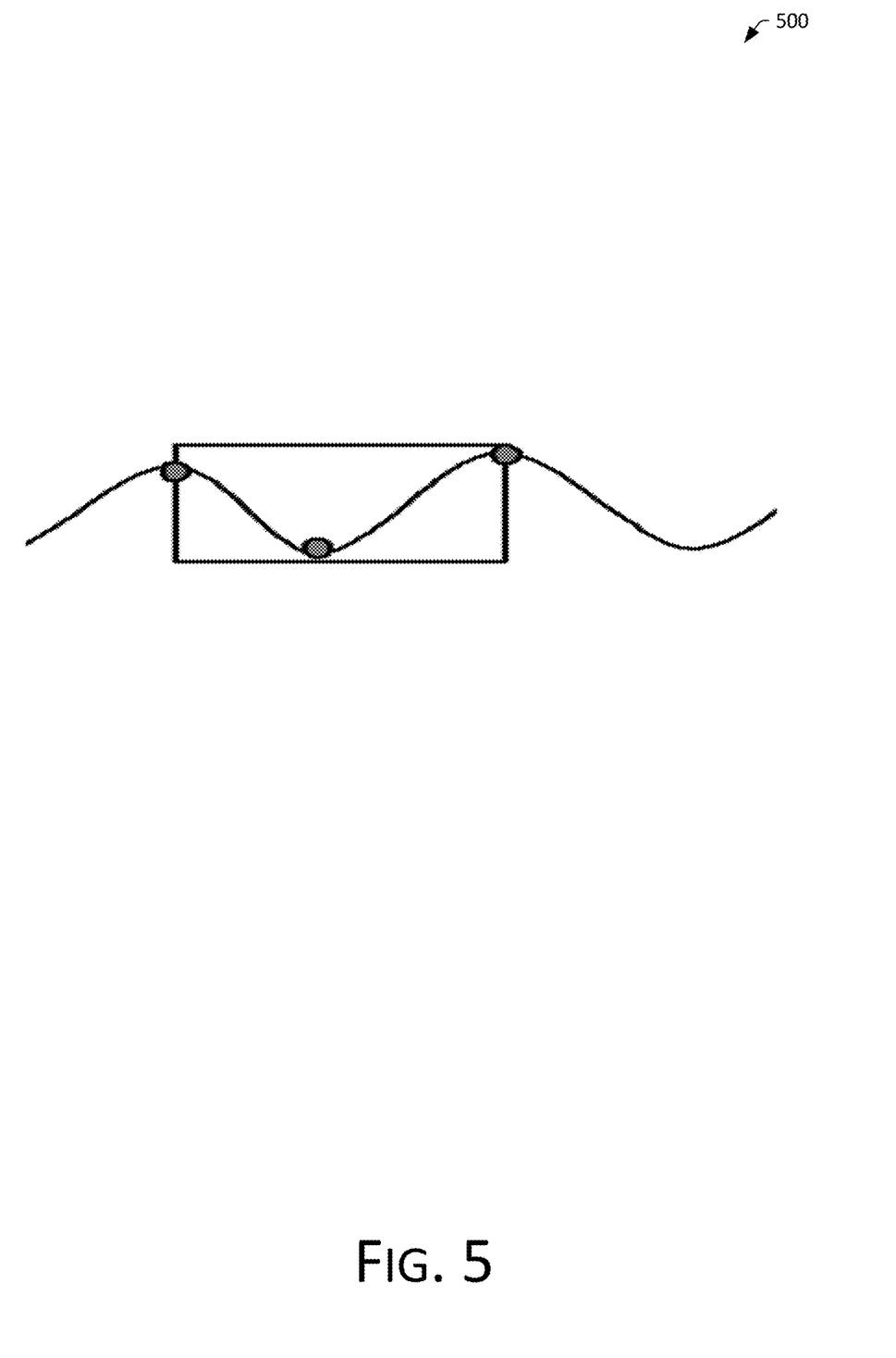
FIG. 5 is a schematic diagram of a maximum value appearing at a left border of a sliding window according to the embodiments of the present disclosure.

Furthermore, in a situation as shown in FIG. 4 or FIG. 5, a minimum value (as shown in FIG. 4) or a maximum value (as shown in FIG. 5) in filtered acceleration values (label 400 in FIG. 4 or label 500 in FIG. 5) appears at a left border (the left-hand side of a block shown in FIG. 4 or FIG. 5) of a sliding window (the block shown in FIG. 4 or FIG. 5). Specifically, a time point corresponding to the minimum value or the maximum value in the filtered acceleration values is a start point of the current step-counting period, and special processing is needed for this situation. Otherwise the step-counting result may have errors, i.e., extra extremum pair(s) may be counted in this situation. Accordingly, for each extremum pair, before the extremum pair is obtained as a valid extremum pair, a determination is needed to be made as to whether a time point corresponding to a maximum value or a minimum value in the extremum pair is a start point of the current step-counting period. If a determination result is negative, this means that the maximum value or the minimum value in the extremum pair does not appear at the start point of the current step-counting period. Thus, the extremum pair may be obtained as a valid extremum pair when absolute values of the maximum value and the minimum value in the extremum pair are located in the extremum range and the time defined by the maximum value and the minimum value in the extremum pair is located in the time range. If the determination result is affirmative, the extremum pair may be discarded, and the extremum pair is not used as a valid extremum pair, regardless of whether the absolute values of the maximum value and the minimum value in the extremum pair are located in the extremum range and whether the time defined by the maximum value and the minimum value in the extremum pair is located in the time range.

It should be noted that determining whether a time point corresponding to a maximum value or a minimum value in an extremum pair is a start point of a current step-counting period determining whether absolute values of the maximum value and the minimum value in the extremum pair are both located in an extremum range, and determining whether a time defined by the extremum pair is located in a time range may be executed in any random order, and may also be executed in parallel.

S206 determines that a user moves by one step in a time defined by a valid extremum pair each time when the valid extremum pair is obtained, and obtains an angular velocity value collected in the time defined by the valid extremum pair from filtered angular velocity values.

S208 calculates a distance and a direction of movement of the user in a current step-counting period based on the movement of the user in the time defined by the valid extremum pair and the angular velocity value collected in the time defined by the valid extremum pair.

Each time when a valid extremum pair is obtained, a determination is made that the user moves by one step in the time defined by the valid extremum pair. During the movement of the user, the direction is also generally changed in addition to the moving distance. Therefore, when determining that the user moves by one step, the positioning device may also obtain an angular velocity value collected in the time defined by the valid extremum pair as a moving direction of the user from among the filtered angular velocity values.

In implementations, when angular velocity values are collected, information such as respective times when the angular velocity values are collected may also be recorded in addition to the collected angular velocity values. Accordingly, the positioning device may search among filtered angular velocity values according to the time range defined by the maximum value and the minimum value in the valid extremum pair, to obtain angular velocity value(s) collected in the time.

It should be noted that no angular velocity value collected in the time defined by the valid extremum pair can possibly be found if a frequency of collecting the angular velocity values is too low. In that case, miss-report may occur, i.e., one step of movement of the user is ignored while the user has indeed moved by one step in reality due to the absence of an angular velocity value. In order to avoid this type of miss-report and improve the positioning accuracy, an angular velocity value collected in a time defined by a previous valid extremum pair is angle-shifted if the filtered angular velocity values do not include an angular velocity value collected in the time defined by the valid extremum pair, and the shifted angular velocity value is used as the angular velocity value generated in the time defined by the current valid extremum pair. Optionally, the shifted angular velocity value may be filled into a corresponding position in the filtered angular velocity values to supplement the angular velocity values.

It should be noted that angle-shifting of an angular velocity value collected in a time defined by a previous valid extremum pair may be angle-shifting of angular velocity values collected in respective times defined by one or more valid extremum pairs prior to a current valid extremum pair. The one or more valid extremum pairs prior to the current valid extremum pair may all belong to a current step-counting period, and may alternatively belong to different step-counting periods.

In implementations, the angle-shifting may be shifting an angular velocity value collected in a time defined by a previous valid extremum pair according to a clockwise direction. For example, a preset shift angle may be 3 degrees. An angular velocity value collected in a time defined by a previous valid extremum pair may then be shifted by 3 degrees according to the clockwise direction. The present disclosure, however, is not limited to this shift angle.

After the above processing, whether the user moves in the time defined by the valid extremum pair and the direction of movement may be obtained. Accordingly, the number of steps of movement of the user in the current step-counting period and the direction of each movement may be obtained statistically, and then the distance and the direction of the movement of the user in the current step-counting period may be calculated.

For example, an average moving speed of a user may be calculated for the user, based on a distance and a number of steps of movement calculated in a previous step-counting period. Accordingly, a distance of movement of the user in a current step-counting period may be obtained based on a number of steps of movement of the user in the current step-counting period and the average moving speed of the user. Based on the distance of movement of the user in the current step-counting period and the moving direction of the user, the distance of the movement of the user in the current step-counting period may be decomposed into an increment ($\Delta x$) in a X direction and an increment ($\Delta y$) in a Y direction. Current position information of the user may then be corrected based on the increment ($\Delta x$) in the X direction and the increment ($\Delta y$) in the Y direction to achieve accurate positioning of the user.

In implementations, the current position information of the user may be obtained through a wireless signal (e.g., Bluetooth, wifi), or based on a base station, or through other existing positioning methods. Existing positioning methods are not described in details in the present disclosure, and reference may be made to related technologies.

In addition, indoor positioning scenarios are relatively complex. Based a horizontal movement, a user may also take an escalator, for example, from the first floor to the third floor. In other words, besides a possible movement in the horizontal direction, the user may also move in the vertical direction. The vertical direction is denoted as a Z direction in the present disclosure.

With the development of sensor technologies, terminal devices have started to include an air pressure sensor. An air pressure sensor may detect an air pressure value of the environment where a terminal device is located. The height between floors of a residential building is generally 2.8-3.0 meters, and the height between floors of an office building is generally about 3.3 meters. In particular, the height between floors of a dormitory building where bunk beds are used is generally 3.6 meters, and the height between floors of a commercial building according to decoration standards is generally greater than 3.9 meters. The air pressure sensor currently can detect a change in air pressures in a distance of about 3 meters, and generally the third and fourth digits after the decimal point change prominently. As can be seen, floor determination via the air pressure sensor is therefore feasible. Accordingly, in order to position a user more accurately, the present disclosure may further include estimating a floor at which the user is located based on changes in air pressure in the environment where the terminal device is located.

In implementations, air pressure values of the environment where the terminal device is located may be collected in the current step-counting period. An average rate of change of air pressure in the environment where the terminal device is located is calculated based on the collected air pressure values. A determination may be made that a floor where the user holding the terminal device is located is changed when the calculated average rate of change of air pressure is greater than a preset threshold. Furthermore, the floor where the user is located may be estimated based on a change in amplitude of air pressure in the environment where the terminal device is located.

In implementations, taking into account of the relatively large influence of temperature on a value of an air pressure, values of the air pressure collected by an air pressure sensor may not be very accurate. However, since the present disclosure performs floor determination by calculating an average rate of change of air pressure instead of using an air pressure value directly, a floor where a user is located can be accurately determined without the need of an absolutely accurate value for the air pressure.

In view of the above, on the one hand, the present disclosure uses multiple types of sensor data to implement multi-information fusion, thereby facilitating an improvement in the accuracy of positioning due to a relatively large amount of information. On the other hand, filtering is performed for the multiple types of sensor data to remove noises included in the sensor data, thereby further improving the accuracy of positioning.

It should be noted that the foregoing method embodiments mentioned are described as a combination of a series of actions for ease of description. One skilled in the art, however, should understand that the present disclosure is not limited to the orders of actions described herein. This is because some operations may be performed in other orders or in parallel according to the present disclosure. Furthermore, one skilled in the art should also understand that the embodiments described in the disclosure are all exemplary embodiments. Actions and modules involved therein may not be essential in the present disclosure.

In the foregoing embodiments, the embodiments have different points of focus in their descriptions. A portion that is not described in detail in a certain embodiment can be referred to a related description in other embodiments.

Figure 6:
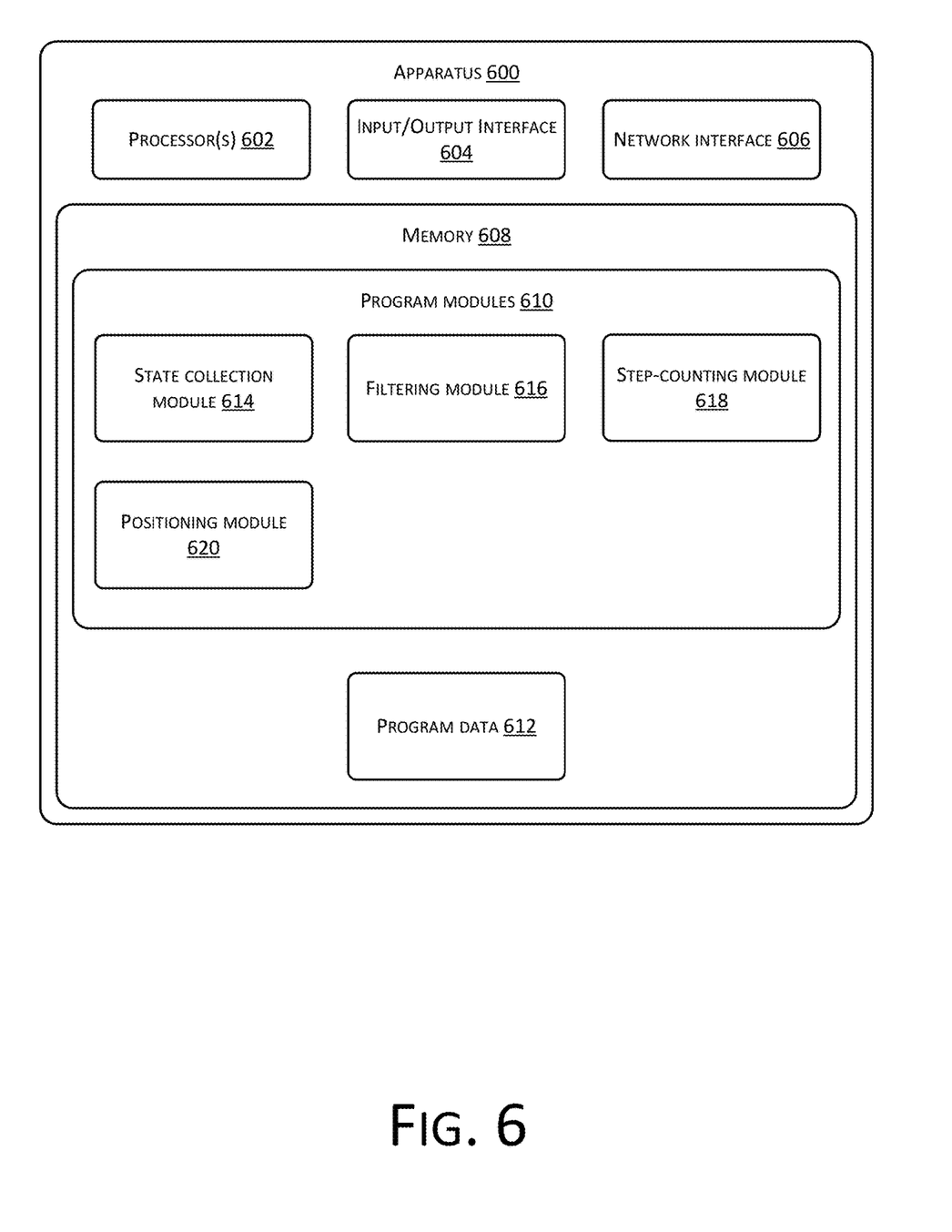
FIG. 6 is a structural diagram of a positioning apparatus according to the embodiments of the present disclosure.

FIG. 6 is a structural diagram of a positioning apparatus 600 according to another embodiment of the present disclosure. In implementations, the positioning apparatus 600 may include one or more computing devices located locally or distributed among different network locations and connected via a network. By way of example and not limitation, the apparatus 600 may include one or more processors 602, an input/output (I/O) interface 604, a network interface 606, and memory 608 as shown in FIG. 6.

The memory 608 may include a form of computer-readable media, e.g., a non-permanent storage device, random-access memory (RAM) and/or a nonvolatile internal storage, such as read-only memory (ROM) or flash RAM. The memory 608 is an example of computer-readable media.

The computer-readable media may include a permanent or non-permanent type, a removable or non-removable media, which may achieve storage of information using any method or technology. The information may include a computer-readable instruction, a data structure, a program module or other data. Examples of computer storage media include, but not limited to, phase-change memory (PRAM), static random access memory (SRAM), dynamic random access memory (DRAM), other types of random-access memory (RAM), read-only memory (ROM), electronically erasable programmable read-only memory (EEPROM), quick flash memory or other internal storage technology, compact disk read-only memory (CD-ROM), digital versatile disc (DVD) or other optical storage, magnetic cassette tape, magnetic disk storage or other magnetic storage devices, or any other non-transmission media, which may be used to store information that may be accessed by a computing device. As defined herein, the computer-readable media does not include transitory media, such as modulated data signals and carrier waves.

In implementations, the memory 608 may include program modules 610 and program data 612. The program modules 612 may include a state collection module 614, a filtering module 616, a step-counting module 618, and a positioning module 620.

In implementations, the state collection module 614 may collect at least two types of sensor data that are able to reflect a motion state of a terminal device in a step-counting period in real time. The filtering module 616 may separately filter the at least two types of sensor data collected by the state collection module 614 to obtain filtered sensor data. The step-counting module 618 may count steps of a user holding the terminal device based on the filtered sensor data obtained by the filtering module 616 to obtain a distance and a direction of movement of the user in the step-counting period. The positioning module 620 may correct current position information of the user based on the distance and the direction of the movement of the user in the step-counting period obtained by the step-counting module 618 to achieve positioning of the user.

In implementations, the state collection module 614 may further collect acceleration values and angular velocity values of the terminal device in the step-counting period in real time. Correspondingly, the filtering module 616 may further filter individually the acceleration values and the angular velocity values to obtain filtered acceleration values and filtered angular velocity values.

Accordingly, in implementations, the step-counting module 618 may further obtain adjacent maximum values and minimum values as extremum pairs from the filtered acceleration values, obtain an extremum pair meeting a preset step-counting condition as a valid extremum pair from the extremum pairs, determine that the user moves by one step in a time defined by the valid extremum pair each time when a valid extremum pair is obtained, obtain an angular velocity value collected in the time defined by the valid extremum pair from the filtered angular velocity values, and calculate the distance and the direction of the movement of the user in the step-counting period based on the movement of the user in the time defined by the valid extremum pair and the angular velocity value collected in the time defined by the valid extremum pair.

Furthermore, in implementations, the step-counting condition may include an extremum range and a time range. Accordingly, in implementations, the step-counting module 618 may determine whether absolute values of a maximum value and a minimum value in a respective extremum pair are both located in the extremum range and whether a time defined by the respective extremum pair is located in the time range for each extremum pair, and obtain the respective extremum pair as the valid extremum pair if determination results thereof are both affirmative.

Furthermore, when obtaining the angular velocity value collected in the time defined by the valid extremum pair from the filtered angular velocity values, the step-counting module 618 may further angle-shift an angular velocity value collected in a time defined by a previous valid extremum pair if the filtered angular velocity values do not include any angular velocity value collected in the time defined by the valid extremum pair, and use the shifted angular velocity value as the angular velocity value generated in the time defined by the valid extremum pair.

Furthermore, when obtaining the valid extremum pair, the step-counting module 618 may further determine whether a time point corresponding to the maximum value or the minimum value in the respective extremum pair is a start point of the step-counting period for each extremum pair, and discard the respective extremum pair if a determination result thereof is affirmative.

For example, after determining that the time point corresponding to the maximum value or the minimum value in the extremum pair is not the start point of the step-counting period, the step-counting module 618 may continue to determine whether absolute values of the maximum value and the minimum value in the extremum pair are both located in the extremum range and whether the time defined by the extremum pair is located in the time range; and obtain the extremum pair as the valid extremum pair if determination results thereof are both affirmative.

Additionally or alternatively, the step-counting module 618 may determine whether absolute values of the maximum value and the minimum value in the extremum pair are both located in the extremum range, and determine whether the time defined by the extremum pair is located in the time range. If determination results thereof are both positive, the step-counting module 618 may continue to determine whether the time point corresponding to the maximum value or the minimum value in the extremum pair is the start point of the step-counting period, and obtain the extremum pair as the valid extremum pair if a determination result thereof is negative, or discard the extremum pair if the determination result is positive.

Figure 7:
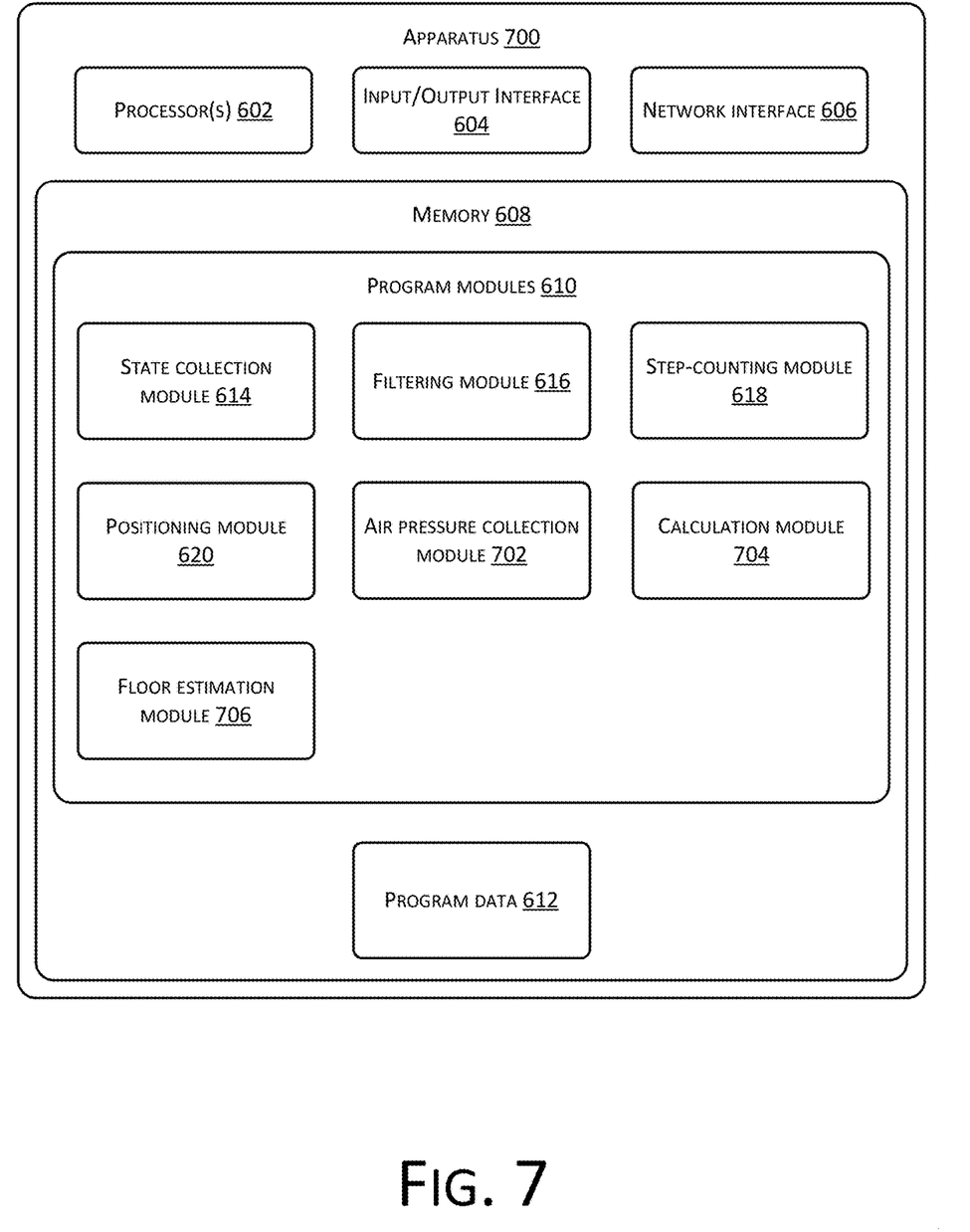
FIG. 7 is a structural diagram of another positioning apparatus according to the embodiments of the present disclosure.

In implementations, the positioning apparatus 700 may further include an air pressure collection module 702, a calculation module 704, and a floor estimation module 706 as shown in FIG. 7. The air pressure collection module 702 may collect air pressure value(s) of an environment where the terminal device is located in the step-counting period. The calculation module 704 may calculate an average rate of change of air pressure in the environment where the terminal device is located based on the air pressure value(s) collected by the air pressure collection module 702. The floor estimation module 706 may determine that a floor where the user is located is changed in response to the average rate of change of air pressure calculated by the calculation module 704 being greater than a preset threshold, and estimate the floor where the user is located based on an amplitude of change of the air pressure in the environment where the terminal device is located.

The positioning apparatus provided in the present disclosure collects at least two types of sensor data that can reflect a motion state of a terminal device in a step-counting period in real time, filters the collected sensor data, and counts steps of a user holding the terminal device based on the filtered sensor data to obtain a distance and a direction of movement of the user in the step-counting period, thereby correcting current position information of the user and thus achieving positioning of the user. On the one hand, the example positioning apparatus uses multiple types of sensor data to implement multi-information fusion, thereby being conducive to improving the positioning accuracy due to the relatively abundant amount of information. On the other hand, filtering is performed on the multiple types of sensor data to remove noises included in the sensor data, thereby being conducive to improving the positioning accuracy.

One skilled in the art can clearly understand that the details of working processes of the systems, apparatuses, and units described above may be obtained with reference to corresponding processes in the foregoing method embodiments for the ease of descriptions, and are not repeatedly described herein.

In the foregoing embodiments provided in the present disclosure, it should be understood that the disclosed systems, apparatuses, and methods may be implemented in other manners. For example, the apparatus embodiments described above are merely illustrative. For example, the above division of units is merely division of logic functions, and other ways of division may exist in real implementation. For instance, multiple units or components may be combined or may be integrated into another system. Some features may be omitted or may not be executed. Furthermore, the displayed or described mutual couplings, direct couplings or communication connections may be indirect couplings or communication connections through some interfaces, apparatuses or units, and may be electrical, mechanical or in other forms.

The units described as separated components may or may not be physically separated, and the components displayed as units may or may not be physical units, i.e., may be located at the same place, or distributed among multiple network units. The objectives of the solutions of the embodiments may be implemented by selecting a part or all of the units according to actual needs.

In addition, the various functional units in the embodiments of the present disclosure can be integrated in a single processing unit. Alternatively, each unit may exist as a physically individual entity. Alternatively, two or more units may be integrated as a single unit. The integrated unit may be implemented in a form of hardware, and may also be implemented in a form of hardware and software functional unit(s).

An integrated unit implemented in a form of a software functional unit may be stored in a computer readable storage media. The software functional unit is stored in a storage media, and includes instructions used to cause computing device(s) (which may include a personal computer, a server, a network device, etc.) or processor(s) to execute some operations of the methods embodiments of the present disclosure. The storage media may include a USB flash disk, a mobile hard disk, a Read-Only Memory (ROM), a Random Access Memory (RAM), a magnetic disk, an optical disc, for example.

Finally, it should be noted that the foregoing embodiments are merely used for describing the technical solutions of the present disclosure, instead of limiting the present disclosure. Although the present disclosure is described in details with reference to the foregoing embodiments, one of ordinary skill in the art should understand that modifications can be made to the technical solutions described in the foregoing embodiments, or perform equivalent replacements for a part of technical features thereof. These modifications or replacements do not cause the essence of the corresponding technical solutions to depart from the spirit and scope of the technical solutions of the embodiments of the present disclosure.

What is claimed is:

1. A method implemented by one or more computing devices, the method comprising:
   collecting at least acceleration values and angular velocity values of a terminal device in a step-counting period in real time;
   filtering the acceleration values and the angular velocity values to obtain filtered acceleration values and filtered angular velocity values;
   counting steps of a user holding the terminal device by:
      obtaining adjacent maximum values and minimum values as extremum pairs from the filtered acceleration values;
      obtaining an extremum pair meeting a preset step-counting condition as a valid extremum pair from the extremum pairs;
      determining that the user moves by one step in a time defined by the valid extremum pair;
      angle-shifting an angular velocity value collected in a time defined by a previous valid extremum pair in response to the filtered angular velocity values including no angular velocity value that is collected in the time defined by the valid extremum pair;
      using the shifted angular velocity value as the angular velocity value in the time defined by the valid extremum pair; and
      calculating a distance and a direction of movement of the user in the step-counting period based at least in part on movement of the user in the time defined by the valid extremum pair and the angular velocity value collected in the time defined by the valid extremum pair; and
   correcting current position information of the user based at least in part on the distance and the direction of the movement of the user in the step-counting period.

2. The method of claim 1, wherein the step-counting condition comprises an extremum range and a time range, and wherein obtaining the extremum pair meeting the preset step-counting condition as the valid extremum pair comprises:

determining whether absolute values of a maximum value and a minimum value in a respective extremum pair are both located in the extremum range and whether a time defined by the respective extremum pair is located in the time range for each extremum pair of the extremum pairs; and obtaining the respective extremum pair as the valid extremum pair in response to both determination results are affirmative.

3. The method of claim 2, further comprising:

determining whether a time point corresponding to the maximum value or the minimum value in the respective extremum pair is a start point of the step-counting period; and discarding the respective extremum pair in response to a determination result is affirmative.

4. The method of claim 1, further comprising:

collecting one or more air pressure values of an environment where the terminal device is located in the step-counting period;

calculating an average rate of change of air pressure in the environment where the terminal device is located based at least in part on the one or more air pressure values;

determining that a floor where the user is located is changed when the average rate of change of air pressure is greater than a preset threshold; and estimating the floor where the user is located based at least in part on an amplitude of change of the air pressure in the environment where the terminal device is located.

5. An apparatus comprising:

one or more processors;

memory;

a state collection module stored in the memory and executable by the one or more processors to collect at least acceleration values and angular velocity values of a terminal device in a step-counting period in real time;

a filtering module stored in the memory and executable by the one or more processors to filter the acceleration values and the angular velocity values to obtain filtered acceleration values and filtered angular velocity values;

a step-counting module stored in the memory and executable by the one or more processors to step-count a user holding the terminal device by:

obtain adjacent maximum values and minimum values as extremum pairs from the filtered acceleration values;

obtain an extremum pair meeting a preset step-counting condition as a valid extremum pair from the extremum pairs;

determine that the user moves by one step in a time defined by the valid extremum pair;

angle-shift an angular velocity value collected in a time defined by a previous valid extremum pair in response to the filtered angular velocity values including no angular velocity value that is collected in the time defined by the valid extremum pair, and use the shifted angular velocity value as the angular velocity value in the time defined by the valid extremum pair; and calculate a distance and a direction of movement of the user in the step-counting period based at least in part on movement of the user in the time defined by the valid extremum pair and the angular velocity value collected in the time defined by the valid extremum pair; and a positioning module stored in the memory and executable by the one or more processors to correct current position information of the user based at least in part on the distance and the direction of the movement of the user in the step-counting period.

6. The apparatus of claim 5, wherein the step-counting condition comprises an extremum range and a time range, and wherein the step-counting module is further configured to:

determine whether absolute values of a maximum value and a minimum value in a respective extremum pair are both located in the extremum range and whether a time defined by the respective extremum pair is located in the time range for each extremum pair of the extremum pairs, and obtain the respective extremum pair as the valid extremum pair in response to both determination results are affirmative.

7. The apparatus of claim 6, wherein the step-counting module is further configured to:

determine whether a time point corresponding to the maximum value or the minimum value in the respective extremum pair is a start point of the step-counting period, and discard the respective extremum pair in response to a determination result is affirmative.

8. The apparatus of claim 5, further comprising:

an air pressure collection module stored in the memory and executable by the one or more processors to collect one or more air pressure values of an environment where the terminal device is located in the step-counting period;

a calculation module stored in the memory and executable by the one or more processors to calculate an average rate of change of air pressure in the environment where the terminal device is located based at least in part on the one or more air pressure values; and a floor estimation module stored in the memory and executable by the one or more processors to determine that a floor where the user is located is changed when the average rate of change of air pressure is greater than a preset threshold, and estimate the floor where the user is located based at least in part on an amplitude of change of the air pressure in the environment where the terminal device is located.

9. One or more computer-readable media storing executable instructions that, when executed by one or more processors, cause the one or more processors to perform acts comprising:

collecting at least acceleration values and angular velocity values of a terminal device in a step-counting period in real time;

filtering the acceleration values and the angular velocity values to obtain filtered acceleration values and filtered angular velocity values;

counting steps of a user holding the terminal device by:

obtaining adjacent maximum values and minimum values as extremum pairs from the filtered acceleration values;

obtaining an extremum pair meeting a preset step-counting condition as a valid extremum pair from the extremum pairs;

determining that the user moves by one step in a time defined by the valid extremum pair;

angle-shifting an angular velocity value collected in a time defined by a previous valid extremum pair in response to the filtered angular velocity values including no angular velocity value that is collected in the time defined by the valid extremum pair;

using the shifted angular velocity value as the angular velocity value in the time defined by the valid extremum pair; and calculating a distance and a direction of movement of the user in the step-counting period based at least in part on movement of the user in the time defined by the valid extremum pair and the angular velocity value collected in the time defined by the valid extremum pair; and correcting current position information of the user based at least in part on the distance and the direction of the movement of the user in the step-counting period.

10. The one or more computer-readable media of claim 9, wherein the step-counting condition comprises an extremum range and a time range, and wherein obtaining the extremum pair meeting the preset step-counting condition as the valid extremum pair comprises:

determining whether absolute values of a maximum value and a minimum value in a respective extremum pair are both located in the extremum range and whether a time defined by the respective extremum pair is located in the time range for each extremum pair of the extremum pairs; and obtaining the respective extremum pair as the valid extremum pair in response to both determination results are affirmative.

11. The one or more computer-readable media of claim 9, the acts further comprising:

collecting one or more air pressure values of an environment where the terminal device is located in the step-counting period;

calculating an average rate of change of air pressure in the environment where the terminal device is located based at least in part on the one or more air pressure values;

determining that a floor where the user is located is changed when the average rate of change of air pressure is greater than a preset threshold; and estimating the floor where the user is located based at least in part on an amplitude of change of the air pressure in the environment where the terminal device is located.

* * * * *